United States Patent
Habets et al.

(10) Patent No.: US 9,459,945 B2
(45) Date of Patent: Oct. 4, 2016

(54) SOFTWARE BUG AND PERFORMANCE DEFICIENCY REPORTING SYSTEM

(75) Inventors: Raymond Joseph Elisabeth Habets, Eindhoven (NL); Rutger Nijlunsing, Veldhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 673 days.

(21) Appl. No.: 13/139,590

(22) PCT Filed: Nov. 19, 2009

(86) PCT No.: PCT/IB2009/055191
§ 371 (c)(1),
(2), (4) Date: Jun. 14, 2011

(87) PCT Pub. No.: WO2010/070490
PCT Pub. Date: Jun. 24, 2010

(65) Prior Publication Data
US 2011/0238768 A1    Sep. 29, 2011

Related U.S. Application Data

(60) Provisional application No. 61/138,592, filed on Dec. 18, 2008.

(51) Int. Cl.
*G06F 11/07* (2006.01)
*G06F 15/16* (2006.01)
*G06F 19/00* (2011.01)

(52) U.S. Cl.
CPC ....... *G06F 11/0748* (2013.01); *G06F 11/0766* (2013.01); *G06F 19/321* (2013.01); *G06F 19/3406* (2013.01); *G06F 19/3487* (2013.01)

(58) Field of Classification Search
CPC ........ G06F 19/00; G06F 19/30; G06F 19/32; G06F 19/321; G06F 19/322; G06F 19/323; G06F 19/324; G06F 19/325; G06F 19/326; G06F 19/327; G06F 19/328; G06F 19/34; G06F 19/3406; G06F 19/3418; G06F 19/3487; G06Q 50/22; G06Q 50/24

USPC .......................... 709/206, 207, 217, 218, 219
See application file for complete search history.

(56) References Cited

U.S. PATENT DOCUMENTS 6,424,996 B1 * 7/2002 Killcommons et al. ...... 709/206
7,436,311 B2 * 10/2008 Rapaport et al. .......... 340/573.1
(Continued)

FOREIGN PATENT DOCUMENTS

| CN | 101226501 A | 7/2008 |
| CN | 101295332 A | 10/2008 |

OTHER PUBLICATIONS

Intel; Mobile Clinical Assistant-Preliminary User Inerface Optimization Guilde; Oct. 2006; 22 pages.

*Primary Examiner* — Saket K Daftuar

(57) ABSTRACT

A medical image system is disclosed, comprising a medical image processing module (20) and a user comment control module (30). The medical image processing module (20) includes at least a medical image display module (22) and a user comment initiation module (26). The user comment control module (30) includes at least: a screenshot capture module or hook (32) configured to capture a screenshot of operation of the medical image processing module at about a time of receipt of a signal from the user comment initiation module; a screenshot editing module or hook (36) configured to enable user editing of the captured screenshot to generate a user-edited screenshot; and a comment review/editing module or hook (40) configured to automatically generate and enable user editing and transmission of an electronic mail message having the user edited screenshot embedded or attached.

18 Claims, 3 Drawing Sheets

(56) References Cited

U.S. PATENT DOCUMENTS

Figure 1:
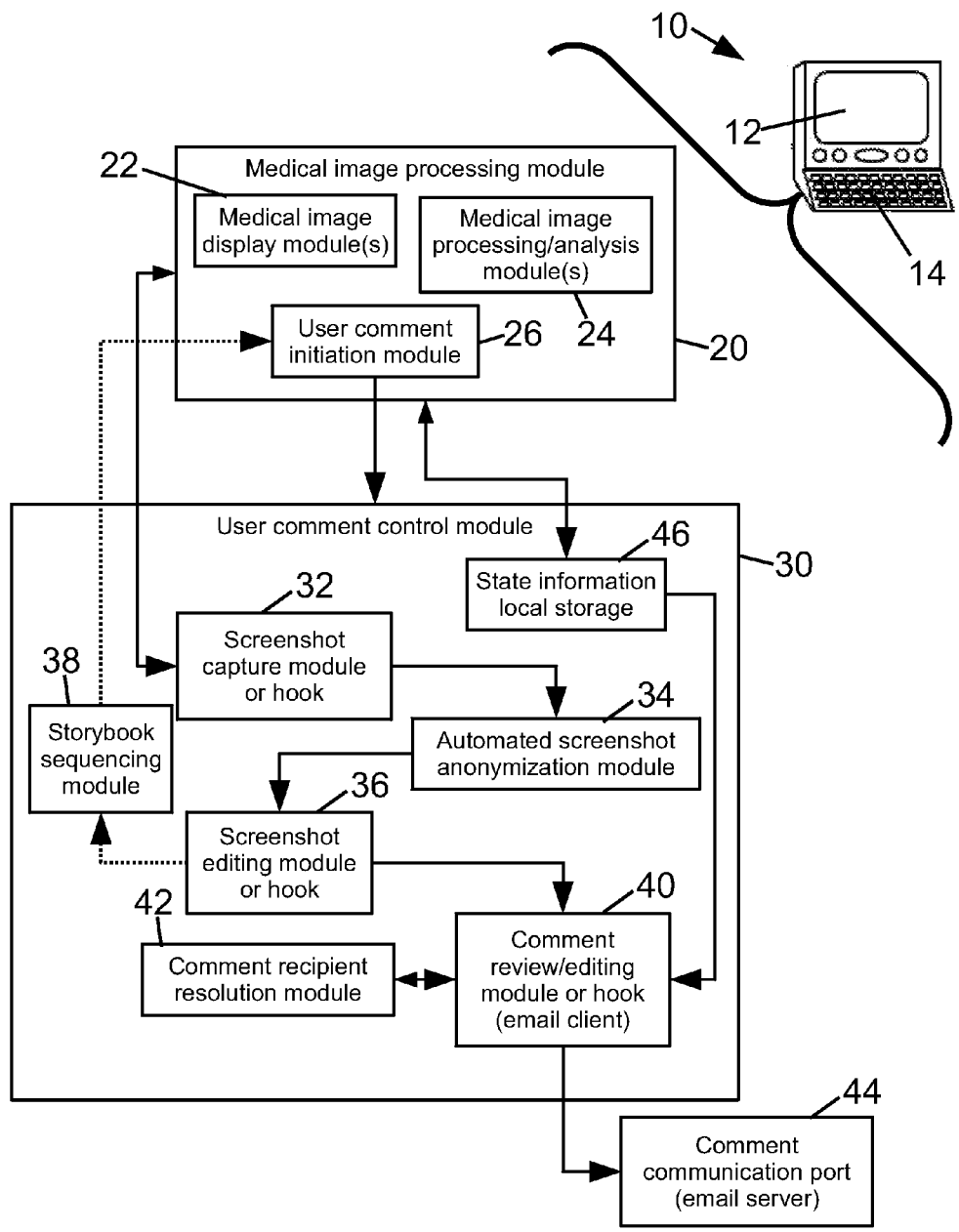

| | | | |
|---|---|---|---|
| 7,444,381 B2* | 10/2008 | Malik | 709/206 |
| 7,499,862 B1* | 3/2009 | Bangalore et al. | 704/275 |
| 7,606,861 B2* | 10/2009 | Killcommons et al. | 709/206 |
| 7,847,970 B1* | 12/2010 | McGrady | G06F 19/3456 345/179 |
| 7,890,573 B2* | 2/2011 | Turner et al. | 709/203 |
| 7,958,100 B2* | 6/2011 | Judd et al. | 707/705 |
| 7,970,625 B2* | 6/2011 | Reicher et al. | 705/2 |
| 8,055,636 B2* | 11/2011 | Judd et al. | 707/705 |
| 8,150,175 B2* | 4/2012 | Natanzon et al. | 382/232 |
| 8,166,381 B2* | 4/2012 | Judd et al. | 715/200 |
| 8,520,978 B2* | 8/2013 | Jakobovits | 382/299 |
| 8,682,042 B1* | 3/2014 | Manion | G06Q 10/00 382/128 |
| 2001/0039502 A1* | 11/2001 | Case | 705/2 |
| 2002/0158912 A1* | 10/2002 | O'Rourke | 345/810 |
| 2002/0173721 A1* | 11/2002 | Grunwald et al. | 600/437 |
| 2004/0054775 A1* | 3/2004 | Poliac et al. | 709/224 |
| 2005/0177312 A1* | 8/2005 | Guerrant | G06F 19/3418 702/19 |
| 2005/0251011 A1* | 11/2005 | Zahlmann et al. | 600/407 |
| 2006/0274928 A1* | 12/2006 | Collins | A61B 6/00 382/132 |
| 2007/0094052 A1* | 4/2007 | Blas | 705/3 |
| 2007/0156692 A1* | 7/2007 | Rosewarne | G06F 17/30861 |
| 2008/0021730 A1* | 1/2008 | Holla et al. | 705/2 |
| 2008/0058611 A1* | 3/2008 | Tsubura | 600/300 |
| 2008/0082966 A1* | 4/2008 | Dorn | G06F 9/545 717/120 |
| 2008/0270438 A1* | 10/2008 | Aronson et al. | 707/101 |
| 2009/0055220 A1* | 2/2009 | Rapaport et al. | 705/2 |
| 2009/0080742 A1* | 3/2009 | Moriya | G06T 19/00 382/131 |
| 2009/0083710 A1* | 3/2009 | Best | G06F 9/4446 717/120 |
| 2009/0087048 A1* | 4/2009 | Takahashi | G06F 19/3487 382/128 |
| 2009/0131746 A1* | 5/2009 | Seo | A61B 1/00045 600/101 |
| 2009/0150484 A1* | 6/2009 | Roberts | 709/203 |
| 2009/0190897 A1* | 7/2009 | Tashiro | H04N 5/76 386/248 |

* cited by examiner

SOFTWARE BUG AND PERFORMANCE DEFICIENCY REPORTING SYSTEM

The following relates to the software arts, medical arts, and related arts. It is described herein with illustrative reference to reporting comments, feature requests, bugs, and so forth that are observed by users of software for medical image display and processing, but will find more general application in reporting of comments, feature requests, bugs, and so forth that are observed by users of software of substantially any kind, such as photographic display and processing software, office suite software, various application software, utility software, and so forth.

Medical image software is used to display and process or analyze medical images acquired by modalities such as magnetic resonance (MR), computed tomography (CT), fluoroscopy, ultrasound, positron emission tomography (PET), single photon emission computed tomography (SPECT), catheter-mounted imagers, and so forth. Medical image software can range from primarily display software, perhaps including features such as zoom/pan, to complex analysis software that performs operations such as spatial registration of images, segmentation to identify or isolate relevant features, filtering to highlight features of interest or to deemphasize irrelevant features, or so forth. Some medical image software is configured to display or process three-dimensional images, for example by displaying selected slices, three-dimensional renderings, maximum intensity projections, or so forth. Some medical image software is configured to display cinematic or "CINE" sequences of images acquired over a period of time to illustrate moving anatomy, influx or wash out of vascular contrast agent, or so forth.

Information derived using medical image software is used to make medical decisions, such as medical diagnoses, treatment modifications, decisions as to whether or not to perform surgery or another interventional operation, and so forth. In some applications, information derived using medical image software is directly used to plan, direct, or control an interventional medical procedure. For example, MR, CT, or another imaging modality is sometimes used in conjunction with suitable medical image software to monitor in real-time the insertion of an interventional instrument into a subject, or to plan and/or monitor a radiation therapy session.

Medical image software developers and maintainers would like to receive substantive feedback from users, both to identify conventional "bugs" (in which the software does not perform as intended) and to identify areas where improvement is possible. As a latter example, an image manipulation control may operate as intended, but users may find the control to be counterintuitive or otherwise difficult to use. Such a situation is not a bug, but it is something about which the medical image software developer or maintainer would like to be informed, so that the software can perhaps be modified to provide a more intuitive or easy-to-use control. Such a situation is referred to herein as a "performance deficiency", rather than a bug. Some bugs or performance deficiencies may not be easily discoverable at the development or maintenance level, and only become apparent to the user, and perhaps even then, only in certain narrowly circumscribed circumstances, such as when performing a particular type of processing (or particular sequence of processing operations) on a particular type of image. To effectively report such a performance deficiency, the user should convey these specific circumstances.

Although it is understood that user feedback is a valuable tool for enhancing medical image software development and maintenance, obtaining such feedback from users can be difficult. Users of medical image software tend to be physicians, radiologists, or other medical specialists having heavy workloads, and it may be difficult to persuade such busy persons to fill out a written bug report, or telephone or email the software developer, or otherwise affirmatively act to provide user feedback.

Providing such feedback can also be difficult due to the visual nature of medical image software. For example, the user may visually perceive that the software is not displaying an image feature correctly, but may find it difficult to convey this information verbally or in writing. In some instances, a system screen capture tool such as the "print screen" key may be used to capture the image. However, system screen capture tools are sometimes unable to capture images generated by specialized medical image software. Even if the system screen capture tool is operative with the medical image software, the resulting screenshot may be of low-resolution or may have other problematic defects. Furthermore, the user may be unfamiliar with the system screen capture tool and may be unable to readily invoke it. By the time the user determines or recalls how to activate the system screen capture, the software state may have changed.

Automated tools such as so-called "crash reports" are also known. These mechanisms collect information about the software state that may be useful in diagnosing a detected software bug. This information is typically in the form of low-level content such as register values, memory dumps, or so forth, and is generally not intelligible to the user. Such automated crash reports are difficult to apply to medical image software due to medical information privacy concerns. The crash report may include patient identity or health-related information in violation of the Health Insurance Portability and Accountability Act (HIPAA) which applies in the United States, or in violation of other relevant patient privacy laws. These same patient privacy concerns may also make medical personnel hesitant to authorize transmitting an automated crash report to the software developer or maintainer. Since the user does not know precisely what information is contained in the crash report, the user may elect to "play it safe" and refuse to authorize transmission of the automated crash report.

Yet another difficulty with automated crash reports is that such reporting mechanisms are typically activated only upon detection of relatively catastrophic flaws such as complete shutdown of the software or a failure to complete execution of a module or function or the like. Accordingly, crash reports are ineffective for reporting non-fatal bugs or performance deficiencies that are not automatically detectable.

Although medical image software is the illustrative software addressed herein, similar problems can arise in the case of other kinds of software. In the case of photographic software, drawing software, presentation preparation software, web browsers, and other visually oriented software, it may be difficult for the user to describe a bug or performance deficiency verbally or in writing. Confidentiality or privacy concerns may also arise in the context of business or professional software, Internet browsers, artistic-related software, and other types of software, again making users reluctant to authorize transmittal of automated bug reports, and again such automated bug reports are limited to reporting automatically detectable bugs.

The following provides new and improved apparatuses and methods which overcome the above-referenced problems and others.

In accordance with one disclosed aspect, a medical image system is disclosed, comprising a medical image processing module and a user comment control module. The medical image processing module includes at least a medical image display module and a user comment initiation module. The user comment control module includes at least: a screenshot capture module or hook configured to capture a screenshot of operation of the medical image processing module at about a time of receipt of a signal from the user comment initiation module; a screenshot editing module or hook configured to enable user editing of the captured screenshot to generate a user-edited screenshot; and a comment review/editing module or hook configured to automatically generate and enable user editing and transmission of an electronic mail message having the user edited screenshot embedded or attached.

In accordance with another disclosed aspect, a digital storage medium is disclosed which stores instructions executable to perform a method comprising: performing medical image processing including at least displaying a medical image; during the performing, receiving a user comment initiation input; capturing a screenshot of the medical image processing at about the time of receipt of the user comment initiation input; performing an editing process to enable a user to edit the screenshot to generate a user-edited screenshot; and communicating the user-edited screenshot to a developer or maintainer of software defining the performed medical image processing.

In accordance with another disclosed aspect, a method is disclosed, comprising: performing user interactive application processing including displaying information to a user on a display; during the performing, receiving a user comment initiation input; capturing a screenshot of the information displayed to the user on the display at about the time of receipt of the user comment initiation input; performing an editing process to enable a user to edit the screenshot to generate a user-edited screenshot, the editing process preferably enabling a user to perform editing operations including at least (i) selecting and redacting portions of the captured screenshot, and (ii) adding text or graphical annotations to the captured screenshot; and communicating the user-edited screenshot to a storage accessible by a developer or maintainer of software defining the performed user interactive application processing.

One advantage resides in providing improved user feedback to a software developer or maintainer.

Another advantage resides in providing improved medical image software through incorporation of user-identified bugs or performance deficiencies.

Another advantage resides in providing intuitive user comment methods and apparatuses that facilitate user reporting of bugs or performance defects to a software developer or maintainer.

Still further advantages will be apparent to those of ordinary skill in the art upon reading and understand the following detailed description.

FIG. 1 diagrammatically shows a medical image processing system employing medical image software and including a user comment sub-system.

Figure 2:
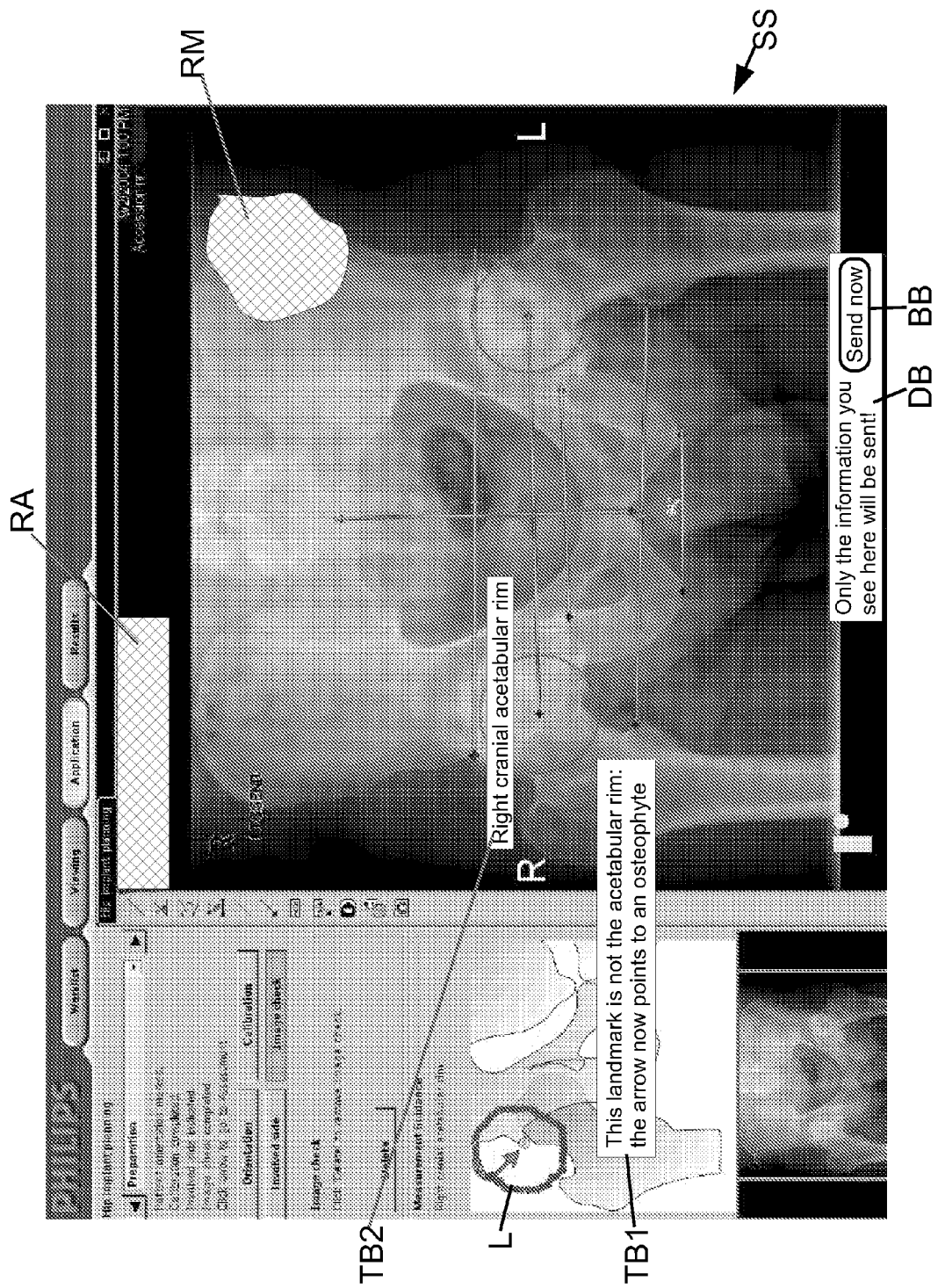

FIG. 2 diagrammatically shows an illustrative user edited screenshot generated by the user comment sub-system of the medical image processing system diagrammatically depicted in FIG. 1.

Figure 3:
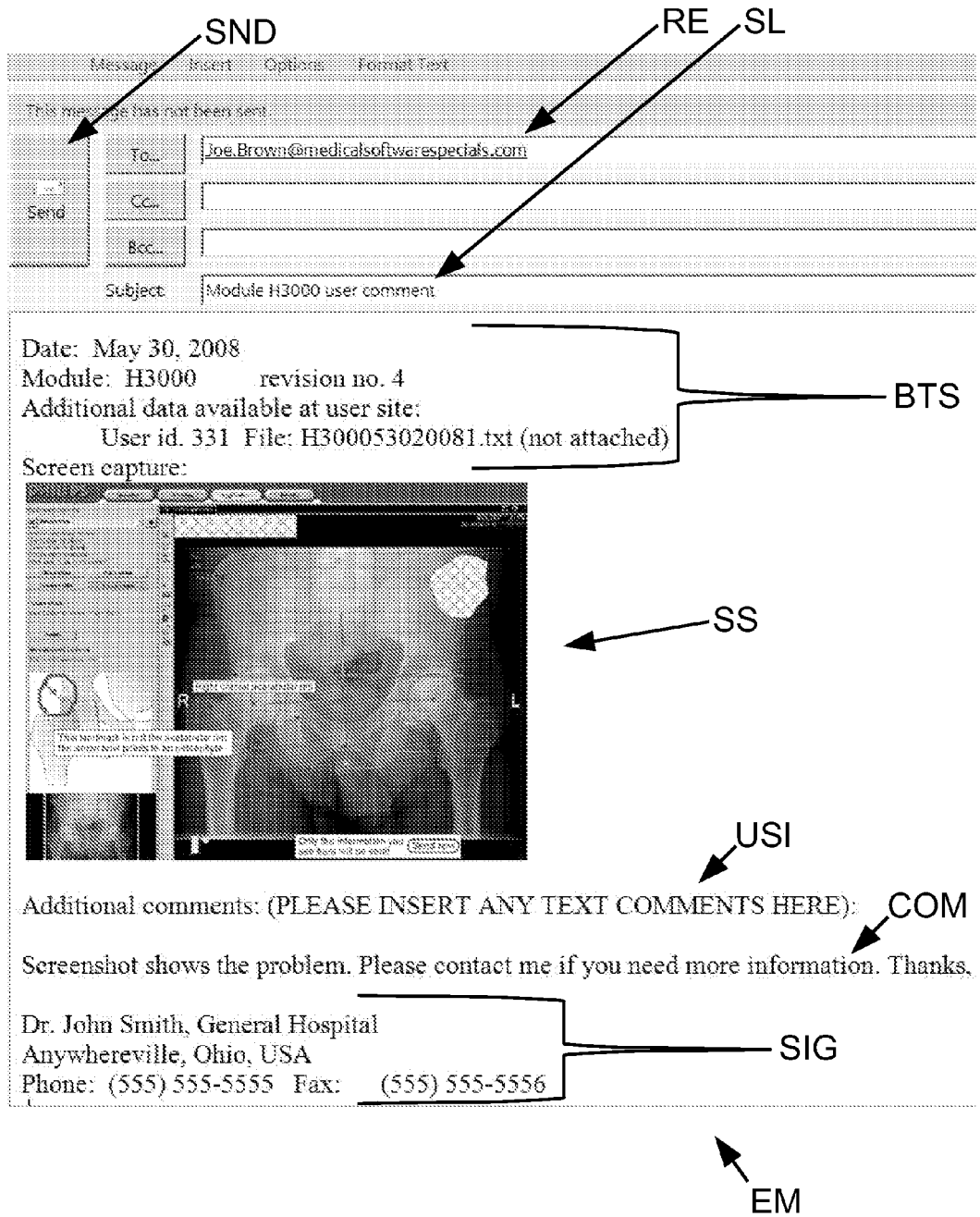

FIG. 3 diagrammatically shows an illustrated electronic mail (email) message including the user-edited screenshot of FIG. 2 embedded therein, said email message having been automatically constructed by the user comment sub-system of the medical image processing system diagrammatically depicted in FIG. 1.

With reference to FIG. 1, a medical image processing system is implemented on an illustrated computer 10 having a display 12 for displaying content including at least medical images in original form and/or after undergoing user-selected processing and further having one or more user input devices such as an illustrated keyboard 14, or a mouse or other pointer-type user input device, or so forth. Optionally, the system may include other components that are not illustrated, such as for example: a printer or other marking engine for generating hardcopies of medical images in original form and/or after undergoing user-selected processing; a medical imaging system such as a computed tomography (CT) imager, a magnetic resonance (MR) imager, a positron emission tomography (PET) imager, a fluoroscope, a gamma camera, or so forth, that is used to acquire medical images of a subject; digital network connectivity components; software for other purposes configured to be executed by the computer 10; or so forth. Moreover, the illustrated computer 10 is optionally replaceable with other digital processing devices capable of executing software, such as a personal data assistant (PDA), "dumb" Internet terminal, or so forth.

The illustrated computer 10 executes instructions stored on a suitable digital storage medium, such as for example a magnetic disk, an optical disk, a random access memory (RAM), a read-only memory (ROM), an electrostatic memory such as a FLASH memory, a remote Internet-based storage device, or so forth. The computer 10 executing said instructions defines a medical image system including a medical image processing module 20 that includes medical image processing components such as an illustrated one or more medical image display modules 22, one or more medical image processing or analysis modules 24, and a user comment initiation module 26. The one or more medical image display or modules 22 are configured to perform tasks such as displaying a medical image (optionally after selected image processing) on the display 12 of the computer 10, and optionally performing selected display manipulation operations such as panning the image, zooming the image in or out, or so forth. As used herein, the term "image processing" is to be broadly construed as encompassing any image rendering or modification process, such as for example: display of an image on the computer display 12 or on another display device; printing of an image using a printer or other marking engine; digital image processing operations such as resizing, cropping, resampling, gray scale or color adjustments, image fusion operations, or the like; image segmenting operations; image annotation operations; image storage format conversion operations; or so forth.

The one or more medical image processing or analysis modules 24 perform tasks responsive to user control inputs, such as for example: image format conversion (e.g., color-to-grayscale conversion, JPEG-to-GIF conversion, or so forth), image filtering operations such as edge filtering, noise reduction filtering or so forth; image rotation operations; color transformation operations; relative spatial registration of different images; combinational operations that subtractively, additively, or otherwise combine images together; image cropping operations; or so forth. The one or more medical image processing or analysis modules 24 may perform general-purpose image processing tasks such as are implemented by image processing software programs such as Adobe Photoshop™ (available from Adobe Systems, Inc., San Jose, Calif., USA) or the GNU Image Manipulation Program (GIMP, available at http://www.gimp.org/ last visited Jun. 3, 2008). The one or more medical image processing or analysis modules 24 may additionally or alternatively perform medical image-specific processing operations, such as for example: conversion of a CT image to a tissue density mapping; automatic image segmentation to identify anatomical features of interest; analysis of a lesion or other feature of interest to determine medically relevant information such as lesion size or weight; or so forth.

It will be appreciated that the one or more medical image display modules 22 and the one or more medical image processing/analysis modules 24 typically operate in a cooperative or synergistic manner to provide the user with feedback as user-selected image processing or analysis operations are performed. For example, an original image may be displayed by the one or more medical image display modules 22, followed by user initiation of an image processing operation by the one or more medical image processing or analysis modules 24 which is automatically followed by an updated display operation performed by the one or more medical image display modules 22 that displays the image after processing, for example by replacing the displayed original image with a display of the processed image, or by displaying the original and processed images side-by-side for easy visual comparison. Similarly, performance of a user-selected analysis operation by the one or more medical image processing or analysis modules 24 is suitably automatically followed by a display operation performed by the one or more medical image display or modules 22 that displays a side-by-side view of the image and analysis results, the latter being suitably displayed as textual, graphical, as an image or map, or in another suitable format, optionally with arrows or other visual links between analysis content and corresponding features of the image if suitable.

As the user performs medical image processing using the medical image processing module 20, the user may encounter a bug or a performance deficiency. Upon doing so, the user invokes the user comment initiation module 26. This invocation can be by a selected user comment initiation input, such as a hotkey (for example, the "F1" function key may be assigned to invoke the user comment initiation module 26), a menu option included in a user selection menu displayed as part of the executing medical image processing module 20, a voice command received via a speech recognition system, or so forth. It is also contemplated for the user comment initiation module 26 to be automatically invoked under certain circumstances, such as responsive to a shutdown of one of the modules 22, 24, or responsive to performance of a newly added operation or feature of the medical image processing module 20 regarding which the software developer or maintainer would like to obtain user feedback, or so forth. However, some bugs and most performance deficiencies are not automatically detectable. Bugs and performance deficiencies are often not readily discernable except during performance of specific user-initiated operations, and moreover what constitutes a "performance deficiency" may be subjective and therefore difficult or impossible to automatically detect (for example, some users may dislike a particular software feature and hence view it as a performance deficiency, while other users may like that same software feature). Accordingly, in cases where a performance deficiency is not objectively determinable, the user comment initiation module 26 is configured to be initiated by a selected hotkey, menu option, or other selectable user comment initiation input.

Activation of the user comment initiation module 26, either automatically or by the selectable user input, causes a user comment control module 30 to activate. The user comment initialization module 26 employs a screenshot-based comment system, and accordingly includes a screenshot capture module or hook 32 configured to capture a screenshot of the medical image processing at about the time of receipt of the user comment initiation input or, more generally, at about the time of receipt of a signal from the user comment initiation module 26, said signal being generated by the user comment initiation module 26 responsive to receipt of the user comment initiation input or, optionally, responsive to an automatic initiation of the module 26 caused by a shutdown or "crash" (i.e., manifestation of an error) of one of the modules 22, 24 or by performance of a newly added operation or feature of the medical image processing module 20 or so forth.

As used herein, the term "hook" refers to instructions executed to cause an associated program to perform a specific process or task. The screenshot capture module or hook 32 is a part of the user comment control module 30. The screenshot capture module or hook 32 is for example defined by stored instructions and is configured to capture screenshots of the performed medical image processing, or alternatively, is defined as only stored instructions that when executed invoke a system screenshot capture function of a computer 10 (independent of the user comment control module 30) to execute the stored instructions. The system screenshot capture function is a general-purpose screenshot capture function that can be used to capture a screenshot of various different programs that may be run on the computer 10. A hook embodiment of the screenshot capture module or hook 32 is configured to invoke the system screenshot capture function for the specific purpose of capturing a screenshot of the medical image processing at about the time of receipt of the user comment initiation input. More generally, a hook may comprise instructions that invoke a general-purpose subroutine, function, dynamic link library (DLL) function, general-purpose helper application, or other available general-purpose tool for the particular purpose of performing an operation related to the medical image processing or to the user comment processing.

The captured screenshot is employed in generating the user comment. In some medical image applications, the screenshot may contain subject-identifying content or private medical information content. For example, the display of the medical image processing application implemented by the medical image processing module 20 may include a standard header listing information such as the subject name and the medical condition of the subject. Transmission of such subject-identifying content or private medical information content may be problematic in view of the HIPAA or other applicable medical privacy laws. Even in the absence of an applicable law, transmission of such subject-identifying content or private medical information content may be problematic in that the subject may object.

Accordingly, an optional automated screenshot anonymization module 34 operates to identify one or more regions of the captured screenshot that contain subject identifying content or private medical information content, and to automatically redact the one or more automatically identified regions. The automatic identification and redaction is suitably performed by the optional anonymization module 34 which is defined by stored instructions. In some embodiments, the identifying of the one or more regions of the captured screenshot that contain subject identifying content or private medical information content is performed based on a priori knowledge of the display layout generated by the medical image processing module 20. For example, it may be known a priori that a displayed panel or window contains patient information that should be redacted, and so the optional anonymization module 34 identifies the one or more regions of the captured screenshot that contain subject identifying content or private medical information content as the region corresponding to the panel or window. As another example, it may be known a priori that the portion of the display containing subject identifying content or private medical information content is rendered using a certain background color, grayscale, or other characteristic, in which case the optional anonymization module 34 identifies the one or more regions of the captured screenshot that contain subject identifying content or private medical information content as those portions of the screenshot having that certain background characteristic.

The automatic redaction operation performed by the optional anonymization module 34 can employ various redaction techniques, such as overwriting the identified region or regions with whitespace, or with black filler, or so forth. Optionally, the automatic redaction can entail replacement of the identified region or regions with other content which is not problematic but which is useful for the user comment task, such as replacing the identified region or regions with date information, medical facility information, or so forth. In general, the automatic redaction entails removal of the original information content from the one or more regions identified as containing subject identifying content or private medical information content, so that such content cannot be inadvertently transmitted to the software developer or maintainer.

The screenshot, after processing by the optional anonymization module 34, is input to a screenshot editing module or hook 36 configured to enable user editing of the captured screenshot to generate a user-edited screenshot. The screenshot editing module or hook 36 is for example, configured to enable a user to perform operations selected from a group consisting of (i) selecting and redacting portions of the captured screenshot, and (ii) adding text or graphical annotations to the captured screenshot. The manual redacting operation (i) enables the user to redact content that may be inappropriate for transmission but which was not identified by the optional anonymization module 34. Such inappropriate content may include, for example: an image feature that is unique to the specific subject, and hence might inadvertently identify the subject; subject identifying content or private medical information content that was not removed by the optional anonymization module 34; information that may identify a confidential study or otherwise disclose confidential information; or so forth. In embodiments in which the optional anonymization module 34 is omitted, the manual redacting operation (i) is the principal mechanism for removal of subject identifying content or private medical information content. The manual redacting operation (i) can also be used for other purposes as chosen by the user, such as redacting content that is irrelevant to the bug or performance deficiency being commented upon by the user.

The term "redaction" (whether automatic as performed by the optional anonymization module 34 or manual as performed with the assistance of the screenshot editing module or hook 36) is to be broadly construed as any operation that removes information or content from the screenshot, and may include: overwriting portions of the screenshot with whitespace or black ink; cropping the screenshot; or so forth.

While the manual redaction operation (i) enables the user to remove information or content from the screenshot, the text or graphical annotation operation (ii) enables the user to add information or content to the screenshot. Such text or graphical annotation is to be broadly construed as including any operation which enables the user to add information or content to the screenshot, and may include for example: adding a textbox to the screenshot including descriptive, explanatory, or other text; adding a manual graphical representation using a stylus, mouse pointer, or other hand-operated input device suitable for assisting the user in adding such manual graphical representation; adding an additional photograph or other digital image onto the screenshot; changing a contrast, brightness or other aspect of a portion of the screenshot so as to highlight that portion; or so forth. In some typical applications of the text or graphical annotation operation (ii), the user may circle or highlight a feature of interest in the screenshot; add text next to a problematic portion of the screenshot identifying or explaining the problem; add text explaining operations performed by the user leading up to the screenshot; or so forth.

The editing operations may employ dedicated image editing instructions that are part of the user comment control module 30, or may employ a hook to a general-purpose image editor or to selected general-purpose image editing functions, subroutines, or the like, or may employ a combination thereof.

In some situations, a single screenshot may be inadequate or less than optimal for the user to convey information about the bug or performance deficiency. In some situations, a sequence of screenshots may be more apropos for conveying the information. Such a sequence of screenshots is referred to herein as a "storybook". For example, if an image registration processing operation is failing to properly (at least in the user's view) register two images, the user may want to describe the situation by providing screenshots including a display of each image separately along display of any input provided in selecting and preparing the images for registration, followed by a screenshot of a display of a fused image that combines the two images after relative registration. Such an explanation may preferably employ at least three screenshots: one for each image alone plus a screenshot of the fused image.

Accordingly, an optional storybook sequencing module 38 is provided. The optional storybook sequencing module 38 is configured to cause iterative looping of user-controlled image processing performed in conjunction with the medical image processing module 20, user-initiated screenshot capture by the user comment initiation module 26 and screenshot capture module or hook 32, optional automatic redaction processing by the optional anonymization module 34, and user editing of each captured screenshot performed in conjunction with the screenshot editing module or hook 36. In this way, the user can generate a sequence or storybook of screenshots that illustrate a sequence of events leading to manifestation of the bug or performance deficiency on which the user wishes to comment. The optional storybook sequencing module 38 includes suitable components (not shown) to support iterative generation of a sequence of user-edited screenshots, said suitable components including, for example: a buffer memory for storing the storybook sequence; user interfacing support such as display of a "finished" button by which the user can indicate that the storybook is complete (said "finished" button optionally being integrated with the screenshot editing module or hook 36 so that after each screenshot is edited the user can select whether or not to continue collecting screenshot captures for the storybook); and so forth.

Once the user completes the screenshot editing process, the edited screenshot (or plurality of edited screenshots in the case of an optional storybook sequence) is input to a comment review/editing module or hook 40 configured to automatically generate and enable user editing and transmission of an electronic mail (email) message having the user-edited screenshot embedded or attached. The comment review/editing module or hook 40 can be embodied as a hook to a general-purpose email client such as, for example, Microsoft Outlook™ (available from Microsoft Corporation, Redmond, Wash., USA), Mail for Leopard™ (available from Apple Corporation, Cupertino, Calif., USA), or the Gnome Evolution email system (available at http://www.gnome.org/projects/evolution/). In such a hook, the comment review/editing hook 40 includes instructions executable to: (i) automatically generate an email message including email header information such as inserting the user's email address in the sender field of the email message (e.g., the "From:" field) and one or more recipient email addresses in a recipient field of the email message (e.g., a "To:" field, or a "cc:" or "bcc:" field) and date/time information, the attached or embedded user-edited screenshot, and optional body text such as instructions to the user, version information relating to the medical image processing software being commented upon, or so forth; and (ii) convey the generated email message to a composition function of the general-purpose email client for user review and optional editing, and initiation and transmission of the email message. Alternatively, the comment review/editing module or hook 40 can be embodied as a module that implements an email client specifically configured for constructing, editing, and initiating conveyance of the email message.

In generating the email message, the one or more recipient email addresses are suitably obtained from local storage or retrieved from a pre-determined location on the Internet or another remote source. An optional comment recipient resolution module 42 can be configured to select one or more recipient email addresses from a local or remote database based on the state of the medical image processing at about the time the user comment initiation module 26 initiated the commenting operation. For example, the comment recipient resolution module 42 may select one or more recipient email addresses corresponding to, for example: the company account manager responsible for contacts between the software vendor (in embodiments in which the software being commented upon is a commercial product) and the hospital or other customer site; one or more individuals or groups assigned to develop or maintain the image processing module that was active at the time the commenting operation was initiated; or so forth. In an alternative approach, a common recipient email address may be used, but the body text of the generated email message may include the name or names of the one or more individuals or groups assigned to develop or maintain the image processing module that was active at the time the commenting operation was initiated, so that at the receiving end suitable sorting software can identify and forward the email message to the appropriate person or persons or group or groups.

The constructed email message optionally provides assurances to the user that the content of the email message is plainly apparent and does not include any hidden information that might reveal the identity or medical information about the subject. To promote such user confidence, the content of the email message is optionally entirely in plaintext, with the user-edited screenshot either embedded as a visible element or attached in a manner that allows the user to display the attached user-edited screenshot. Optionally, the content of the email message may include text providing further assurance, such as text reading: "The content of this message is in plaintext and includes the visible screenshot or screenshots you captured and edited. The information that will be sent will be exactly as shown on this email composition screen."

The comment review/editing module or hook 40 also enables the user to edit content of the automatically generated email message. For example, the body text of the email message is editable to enable the user to add further comments of a textual nature beyond those which may have been added to the user-edited screenshot. For example, the user may not want to overlay a long textual comment annotation onto the screenshot during the screenshot editing process, but a long textual comment can easily be added to the body text of the automatically generated email message during the email message editing process. Optionally, the comment review/editing module or hook 40 may be configured to allow the user to re-invoke the screenshot editing module or hook 36 (or another image editing function) so as to make further annotations or redactions in the attached or embedded screenshot or screenshots. Optionally, the comment review/editing module or hook 40 may be configured to allow the user to add new email recipient addresses or to delete or modify the default email recipient addresses. For example, if the user is based at a hospital, the user may wish to add email addresses corresponding to colleagues at the hospital so that a relevant portion of the hospital staff is made aware of the bug or performance deficiency being commented upon.

Once the user is satisfied with the email message, the user causes the comment review/editing module or hook 40 forward the generated and optionally user-edited email message to a comment communication port 44, such as an email server. In other words, the comment review/editing module or hook 40 is configured to enable the user to initiate transmission of the email message, optionally after user editing. The email server or other comment communication port 44 transmits the email message via the Internet or another digital network to the email recipients identified in the recipient field or fields of the generated and optionally user-edited email message.

Although email-based review and transmission components 40, 42, 44 are illustrated, it is also contemplated to employ other transmission pathways and components. For example, the transmission pathway may employ a dedicated Internet universal resource locator (URL) address (for example, of the form http://www . . . ) that provides an interactive user-fillable form. The generation and review component (corresponding to illustrated elements 40, 42 for the email-based embodiment) are suitably a web browser (either a dedicated browser or a hook such as a plug-in to a general-purpose web browser) along with suitable instructions executable to generate a filled-out form that is filled out with default values in at least some fields of the user-fillable form. The user can edit form fields using the browser, and the user-fillable form suitably includes a "send" button or the like which the user can activate to initiate transmission of the filled out and optionally user-edited form to the software developer or maintainer.

The user comment control module 30 when activated by the user comment initiation module 26 may be optionally capable of collecting information about the state of the executing image processing software, that is, the state of the medical image processing module 20, and storing such state information locally in a state information local storage 46 that is included with or accessible by the user comment control module 30. Optionally, some of this information is incorporated into the body text of the email message generated by the comment review/editing module or hook 40 as plain text or another manifestly user-readable format. Such state information, if incorporated into the generated email message, should be of a nature that does not reveal information that might identify the subject or convey private subject medical information, and is preferably also manifestly readable by the user so that the user can be assured that no confidential information is being conveyed. In another approach, a reference to the locally stored state information (for example, in the form of a filename or the like) is incorporated into the generated email body text, again preferably in plain text or another user-readable format. In this way, if the software developer or maintainer decides that this additional state information is needed to diagnose or analyze the bug or alleged performance deficiency, then the software developer or maintainer can request that the user send that information, thus ensuring that the user maintains control over the state information including any potentially confidential portions of the state information.

Having described with reference to FIG. 1 one illustrative embodiment and optional or alternative features to that embodiment of the medical image system including user commenting functionality, an illustrative example user comment is next described.

With continuing reference to FIG. 1 and with further reference to FIG. 2, an illustrative user-edited screenshot SS is depicted. The illustrative screenshot SS is suitably acquired by the screenshot capture module or hook 32 responsive to a signal from the user comment initiation module 26. The optional anonymization module 34 automatically identifies and automatically redacts a region RA of the screenshot SS that is identified by the anonymization module 34 as containing subject identifying content or private medical information content. The redacted rectangular region RA is identified, for example, based on a priori knowledge that the rectangular region RA is used to display patient name information or the like. An irregular region RM is manually redacted by the user, for example by manually identifying the region RM using a stylus, mouse pointer, or other user input device to draw a line around the irregular region RM and selecting a button, hotkey, or other input indicating redaction. The region RM may, for example, include a distinctive tumor, bone outgrowth, or other distinctive anatomical feature that might identify the subject, or the user may have another reason for redacting the region RM such as concern that it might identify the topic of a study of which the image is a part.

The screenshot SS of FIG. 2 also includes added annotations, such as an identifying circling line L and annotated text boxes TB1, TB2. Additionally, the screenshot editing module or hook 36 superimposes a dialog box DB that informs the user that "Only the information you see here will be sent!" and includes a "Send Now" button BB that initiates input of the user-edited screenshot SS of FIG. 2 to the comment review/editing module or hook 40.

With continuing reference to FIGS. 1 and 2 and with further reference to FIG. 3, the comment review/editing module or hook 40 generates and enables user editing of an email message EM as shown in FIG. 3. The generated email message EM includes the following automatically generated content: a filled-in recipient email address (Joe.Brown@medicalsoftwarespecials.com) RE; a subject line SL containing text that identifies "Module H3000" which is the software module being commented upon; body text state information BTS identifying the date, module H3000, and a local location ("User id. 331 File: H300053020081.txt) where state information can be located along with a reassurance that the actual state file content is not attached; the screenshot SS as an embedded element; body text content USI providing user instructions for optionally providing further textual comments; and body text content SIG identifying user signature information including name, address, and contact information. Although the illustrative state information file identified in the body text state information BTS is a text file (extension *.txt), other formats can be used to store the state information, including optionally proprietary formats, which optionally may store non-text state information such as images, binary register values, or other information pertinent to recreating the system state at the time the user comment was initiated. The email message EM of FIG. 3 also includes a textual comment COM added by the user using the editing capability of the comment review/editing module or hook 40. Furthermore, the comment review/editing module or hook 40 provides control buttons including a "Send" button SND which enables the user to initiate transmission of the comment by transmitting the edited email message via the email server or other comment communication port 44.

The illustrative embodiments have been described in relation to an illustrative medical image system. However, it is to be appreciated that the user comment components 26, 30, 44 and corresponding methods and software as disclosed herein are readily applied to or incorporated with other types of software, such as image processing software in general, graphical art software, office productivity software, Internet browsing software, and so forth. The disclosed user comment components 26, 30, 44 and corresponding methods and software as disclosed herein are advantageous for conveying user comments respective to substantially any type of software, and are of especial advantage for conveying user comments respective to visually oriented software (for example, directed to image processing or graphical art applications or so forth) and software that processes confidential information (such as the illustrative medical software, or financial software, or business software, or so forth).

This application has described one or more preferred embodiments. Modifications and alterations may occur to others upon reading and understanding the preceding detailed description. It is intended that the application be construed as including all such modifications and alterations insofar as they come within the scope of the appended claims or the equivalents thereof.

Having thus described the preferred embodiments, the invention is now claimed to be:

1. A medical image system comprising:
   a computer including a display device, one or more user input devices, and a digital storage medium, the computer configured to run software stored on the digital storage medium to define the medical image system including:
      a medical image processing module executed by the computer including a medical image display module configured to display a medical image on the display device of the computer, the medical image processing module configured to perform image processing of the medical image responsive to user control inputs via the one or more user input devices, wherein the medical image processing module running on the computer generates a display on the display device of the computer including the display of the medical image by the medical image display module, a displayed subject name, and display of non-image information pertaining to the medical image processing performed by the medical image processing module, the medical image processing module further including a user comment initiation module; and a user comment control module executed by the computer including at least:

a screenshot capture module or hook configured to capture a screenshot of the display, on the display device of the computer, of the medical image processing module running on the computer at about a time of receipt of a signal from the user comment initiation module of the medical image processing module wherein the captured screenshot includes the display of the medical image by the medical image display module, the displayed subject name, and the display of the non-image information pertaining to the medical image processing performed by the medical image processing module, a screenshot editing module or hook configured to enable user editing of the captured screenshot to generate a user-edited screenshot, and a comment review/editing module or hook configured to automatically generate and enable user editing and transmission to a developer or maintainer of the medical image system of an electronic mail message having the user-edited screenshot embedded or attached.

2. The medical image system as set forth in claim 1, wherein the user comment control module further comprises:

an automated screenshot anonymization module configured to automatically identify and redact one or more regions of the captured screenshot, including at least the displayed subject name, that contain subject-identifying content or private medical information content.

3. The medical image system as set forth in claim 1, wherein the screenshot editing module or hook is configured to enable a user to perform operations selected from a group consisting of (i) selecting and redacting portions of the captured screenshot, and (ii) adding text or graphical annotations to the captured screenshot.

4. The medical image system as set forth in claim 1, wherein the comment review/editing module or hook is configured to automatically construct an electronic mail message having the user-edited screenshot embedded or attached, and is further configured to enable user editing and transmission of the constructed electronic mail message.

5. A non-transitory digital storage medium storing instructions executable on a computer to perform a method comprising:

performing medical image processing of a medical image by running medical image processing software on the computer that generates a display on a display device of the computer including at least a display of the medical image and a display of non-image information pertaining to the medical image processing;

during the performing, receiving a user comment initiation input;

capturing a screenshot of the medical image processing at about the time of receipt of the user comment initiation input wherein the captured screenshot is of the display on the display device of the computer and includes at least the display of the medical image and the display of non-image information pertaining to the medical image processing;

performing an editing process to enable a user to edit the screenshot to generate a user-edited screenshot; and communicating the user-edited screenshot to a developer or maintainer of software defining the performed medical image processing.

6. The non-transitory digital storage medium as set forth in claim 5, wherein the performed editing process is defined by the stored instructions.

7. The non-transitory digital storage medium as set forth in claim 5, wherein the performed method further comprises:

automatically identifying one or more regions of the captured screenshot that contain subject-identifying content or private medical information content; and automatically redacting the one or more automatically identified regions;

wherein the automatic identifying process and the automatic redacting process are each defined by the stored instructions.

8. The non-transitory digital storage medium as set forth in claim 5, wherein the capturing of a screenshot comprises one of:

invoking a screenshot capture module defined by the stored instructions and configured to capture screenshots of the performed medical image processing, and invoking a system screenshot capture function of a computer executing the stored instructions.

9. The non-transitory digital storage medium as set forth in claim 5, wherein the performed editing process enables a user to (i) select and redact portions of the captured screenshot and (ii) add text or graphical annotations to the captured screenshot.

10. The non-transitory digital storage medium as set forth in claim 5, wherein the communicating comprises:

automatically constructing an electronic mail message having the user-edited screenshot embedded or attached; and performing an electronic mail process enabling user editing and transmission of the constructed electronic mail message;

wherein at least the automatic constructing process is defined by the stored instructions.

11. The digital storage medium as set forth in claim 10, wherein the automatic constructing of the electronic mail message comprises:

automatically inserting into the electronic mail message as user-readable text information pertaining to a state of the performed medical image processing at about the time of receipt of the user comment initiation input.

12. The digital storage medium as set forth in claim 10, wherein said method further comprises:

repeating the capturing and the performing of the editing process to generate a plurality of user-edited screenshots corresponding to different times of the performed user-interactive application processing, the automatic constructing including automatically constructing the electronic mail message having the plurality of user-edited screenshots embedded or attached.

13. The digital storage medium as set forth in claim 10, wherein the automatic constructing of the electronic mail message comprises:

selecting one or more recipient email addresses based on a state of the performed medical image processing about the time of receipt of the user comment initiation input; and inserting the selected one or more recipient email addresses into a recipient field of the electronic mail message.

14. The non-transitory digital storage medium of claim 5 wherein receiving a user comment initiation input comprises detecting a crash of the medical image processing software running on the computer.

15. The medical image system of claim 1 wherein the user comment initiation module is configured to generate the signal in response to an automatic initiation of the user comment initiation module caused by a shutdown or crash of the medical image display module or the medical image processing module.

16. The medical image system of claim 1 wherein the user comment initiation module is configured to generate the signal in response to an automatic initiation of the user comment initiation module caused by performance of a newly added operation or feature of the medical image processing module.

17. A medical image system comprising:
a computer including a display device, one or more user input devices, and a digital storage medium, the computer configured to run:
 a medical image processing program executed by the computer to display a medical image on the display device of the computer and to perform image processing of the medical image responsive to user control inputs via the one or more user input devices, wherein the medical image processing program running on the computer generates a program display on the display device of the computer including the medical image, a subject name, and non-image information pertaining to the medical image processing performed by the running medical image processing program;
 a user comment initiation module executed by the computer to generate a signal in response to an automatic initiation of the user comment initiation module caused by a shutdown or crash of the running medical image processing program; and
 a user comment control module executed by the computer to perform operations including at least (i) capturing a screenshot of the program display generated on the display device of the computer by the running medical image processing program at about a time of receipt of the signal from the user comment initiation module wherein the captured screenshot of the program display includes the medical image, the subject name, and the non-image information pertaining to the medical image processing performed by the medical image processing program, (ii) editing the captured screenshot to generate a user-edited screenshot, and (iii) automatically generating and enabling user editing and transmission to a developer or maintainer of the medical image system of an electronic mail message having the user-edited screenshot embedded or attached.

18. A medical image system comprising:
a computer including a display device, one or more user input devices, and a digital storage medium, the computer configured to run:
 a medical image processing program executed by the computer to display a medical image on the display device of the computer and to perform image processing of the medical image responsive to user control inputs via the one or more user input devices, wherein the medical image processing program running on the computer generates a program display on the display device of the computer including the medical image, a subject name, and non-image information pertaining to the medical image processing performed by the running medical image processing program;
 a user comment initiation module executed by the computer to generate a signal in response to an automatic initiation of the user comment initiation module caused by performance of a newly added operation or feature of the running medical image processing program; and
 a user comment control module executed by the computer to perform operations including at least (i) capturing a screenshot of the program display generated on the display device of the computer by the running medical image processing program at about a time of receipt of the signal from the user comment initiation module wherein the captured screenshot of the program display includes the medical image, the subject name, and the non-image information pertaining to the medical image processing performed by the medical image processing program, (ii) editing the captured screenshot to generate a user-edited screenshot, and (iii) automatically generating and enabling user editing and transmission to a developer or maintainer of the medical image system of an electronic mail message having the user-edited screenshot embedded or attached.

* * * * *